United States Patent [19]

Toyoda et al.

[11] Patent Number: 4,942,178
[45] Date of Patent: Jul. 17, 1990

[54] PLANT PROTECTION AGENTS FOR CONTROL OF FUNGI

[75] Inventors: Shigeaki Toyoda, Wako; Shunnosuke Watanabe, Higashikurume; Hiroshi Tabata, Tokyo, all of Japan

[73] Assignee: Agro-Kanesho Co., Ltd., Tokyo, Japan

[21] Appl. No.: 278,243

[22] Filed: Nov. 30, 1988

[30] Foreign Application Priority Data

Dec. 1, 1987 [JP] Japan .................. 62-304121

[51] Int. Cl.$^5$ .................. A01N 37/18; C07C 233/65
[52] U.S. Cl. .................. 514/617; 514/619; 564/166; 564/184
[58] Field of Search .............. 564/166, 184; 514/619, 514/617

[56] References Cited

U.S. PATENT DOCUMENTS

| | | | |
|---|---|---|---|
| 3,969,510 | 7/1976 | Osicka et al. | 424/324 |
| 4,093,743 | 6/1978 | Yabatani et al. | 424/324 |
| 4,123,554 | 10/1978 | Kawada et al. | 424/324 |

FOREIGN PATENT DOCUMENTS

| | | |
|---|---|---|
| 83339 | 1/1975 | Japan . |
| 148321 | 6/1975 | Japan . |
| 128343 | 3/1977 | Japan . |
| 116344 | 1/1978 | Japan . |
| 9739 | 5/1978 | Japan . |
| 132536 | 10/1978 | Japan . |
| 116343 | 12/1978 | Japan . |
| 107520 | 4/1979 | Japan . |
| 0028909 | 2/1980 | Japan . |
| 55-31048 | 4/1980 | Japan . |
| 55-28909 | 7/1980 | Japan . |
| 49345 | 8/1980 | Japan . |
| 149204 | 4/1982 | Japan . |
| 172448 | 3/1984 | Japan . |
| 7506953 | 12/1975 | Netherlands . |
| 1217868 | 12/1970 | United Kingdom . |

OTHER PUBLICATIONS

*Chemical Abstracts Tenth Collective Index,* Formula Index (1982), p. 10423F; $C_{17}H_{16}F_3NO$.

*Chemical Abstracts,* "Synergistic Fungicides, etc.", vol. 94; 169411m (1981).

*Primary Examiner*—Richard L. Raymond
*Assistant Examiner*—P. O'Sullivan
*Attorney, Agent, or Firm*—Oblon, Spivak, McClelland, Maier & Neustadt

[57] ABSTRACT

Derivatives of 3'-isopropylbenzanilide represented by the following general formula:

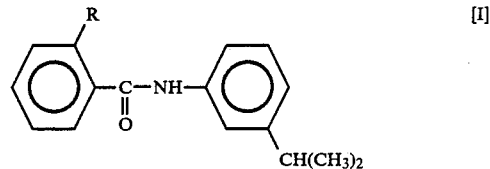

wherein R stands for a trifluoromethyl or nitro group. These compounds are of remarkable utility when used in various plant protection agents for control of fungi.

2 Claims, No Drawings

PLANT PROTECTION AGENTS FOR CONTROL OF FUNGI

BACKGROUND OF THE INVENTION:

1. Field of the Invention:

The present invention relates generally to novel plant protection agents or compositions for control of fungi, and particularly to such compositions containing one or more of derivatives of 3'-isopropylbenzanilide represented by the following general formula (I):

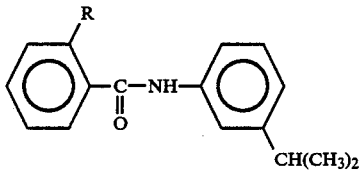

wherein R stands for a trifluoromethyl or nitro group.

2. Prior Art Statement;

Plant protection effects of benzanilide base compounds and their functions as fungicides have been disclosed, for example, in the specification of British Patent No. 1,217,868. The invention disclosed in this prior publication is directed to a plant protection agent for control of fungi, characterized by containing, as an effective component, benzanilide or a derivative thereof represented by the general formula (A) set forth below:

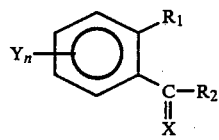

The compounds provided by the present invention are also represented by the general formula (A) wherein $R_1$ is a trifluoromethyl or nitro group, $Y_n$ is a hydrogen atom, X is an oxygen atom, and $R_2$ is $-NR_3R_4$ where $R_3$ stands for a hydrogen atom and $R_4$ stands for a m-isopropylphenyl group. The such compounds are neither specifically disclosed nor suggested in the specification of the British Patent referred to above.

On the other hand, plant protection and fungicidal effects of 3'-isopropylbenzanilide base compounds are disclosed in Japanese Patent Publication No. 12973/1978. The invention described in this publication relates to plant protection agents for control of fungi containing 3'-isopropylbenzanilide represented by the general formula (B):

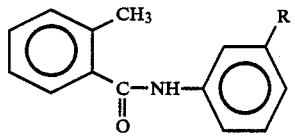

wherein R stands for an alkyl group.

However, the plant protection and fungicidal effects of these known benzanilide base compounds are not always satisfactory, and there is thus a need to develop a further improved plant protection agent for control of fungi.

SUMMARY OF THE INVENTION

The object of this invention is to provide a compound exhibiting improved fungicidal effects over the known benzanilide base compounds as aforementioned, and to provide a plant protection agent for control of fungi containing such a compound.

Through studies on derivatives of 3-isopropylbenzanilide, we have found that the compounds (hereinafter referred to as "compounds of this invention") represented by the general formula (I) set forth above exhibit superior preventive effects against various fungi which may cause plant diseases. In detail, the compounds and compositions provided by the invention exhibit superior inhibition or killing effects, for example, for Rhizoctonia solani which poses problems in rice plant cultivation, Puccinia striiformis of wheats and various other rusts appearing on vegetables and ornamental plants.

DESCRIPTION OF THE INVENTION

The compounds of this invention may be prepared by reacting carboxylic acid chlorides represented by the following general formula (II):

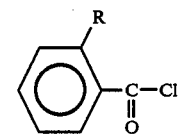

wherein R stands for a trifluoromethyl or nitro group; with 3-isopropylaniline in the presence of a hydrogen halide stripper. Alternatively, the compounds of this invention may be prepared by reacting carboxylic acids represented by the following general formula (III):

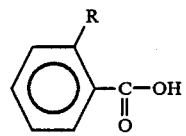

wherein R stands for a trifluoromethyl or nitro group; with 3-isopropylaniline in the presence of a dehydrating agent.

The compounds of the invention may be applied as effective fungicide components not only by treating the cultivated plants directly with them but also by admixing them with solid carriers, liquid carriers, surface active agents or other formulation aids commonly used in agricultural chemicals. More particularly, similar to ordinary agricultural chemicals, they are usually formulated in the form of emulsions, wettable powders, granules, powders or liquid formulations. Solid carriers used in formulating the compounds of the invention into suitable solid formulations include talc, clay, kaolin, white carbon and bentonite of fine powder or granulated form. Usable liquid carriers include aromatic hydrocarbons such as benzene, xylene, and methyl naphthalene, alcohols such as propanol, ethylene glycol and cellosolve, ketones such as acetone and isophorone, vegetable oils such as soybean oil and cotton seed oil, dimethylformamide, dimethylsulfoxide, acetonitrile and water. Surface active agents used for emulsification or dispersification are anionic surfactants such as alkyl sulfuric acid esters, alkyl sulfonates and polyoxyethylenealkylarylether phosphate esters; and non-ionic surfactants such as polyoxyethylene polyoxypropylene block copolymers and polyoxyethylene-sorbitan carboxylate esters. Other formulation aids which may be used to prepare the plant protection agents according to the invention are lignin sulfonates, alginates, polyvinyl-alcohol, CMC and PAP.

When one of the compounds of this invention is used as a plant protection agent, it may be contained in a proper formulation, such as emulsion, wettable powder, granule, powder or liquid form, and dispensed in an amount of from 1 gram to 1000 grams, preferably from 5 grams to 100 grams, per 10 ares based on the dispensed quantity of effective component(s). The compounds of this invention may also be mixed with other fungicides or insecticides with the aim of reducing the work of application or to obtain a mixture capable of exterminating various species of harmful fungi or insects which cause plant diseases.

EXAMPLES

Synthesis examples of the compound of this invention will now described below.

SYNTHESIS EXAMPLE 1

Preparation of 3'-isopropyl-2-trifluoromethylbenzanilide (Compound No. 1)

One gram of 3-isopropylaniline and 0.8 gram of triethylamine were dissolved in 50 ml of THF, cooled to 0° C. and agitated. A solution prepared by dissolving 1.54 grams of 2-trifluoromethylbenzoyl chloride in 20 ml of THF were dropwisely added. After agitating for 30 minutes, the reaction mixture was filtered and THF in the filtrate was distilled off under reduced pressure. The residue was extracted by benzene, and rinsed with 3N-HCl, a saturated sodium bicarbonate solution and water successively in this order. The benzene layer was dried by adding anhydrous magnesium sulfate and then benzene was distilled off under reduced pressure to obtain the desired product. The yield was 1.98 grams (87%), and the product had a melting point of 87.5° to 88.5° C. and an IR absorption peak at 1655 cm$^{-1}$ (c=b 0).

SYNTHESIS EXAMPLE 2

Preparation of 3'-isopropyl-2-nitrobenzanilide (Compound No. 2)

One gram of 3-isopropylaniline and 0.8 gram of triethylamine were dissolved in 50 ml of THF, cooled to 0° C. and agitated. A solution prepared by dissolving 1.37 grams of 2-nitrobenzoyl chloride in 20 ml of THF was dropwisely added. After agitating for 30 minutes, the reaction mixture was filtered and THF in the filtrate was distilled off under reduced pressure. The residue was extracted with benzene, and rinsed with 3N-HCl, a saturated sodium bicarbonate solution and water successively in this order. The benzene layer was dried by adding anhydrous magnesium sulfate and then benzene was distilled off under reduced pressure to obtain the desired product. The yield was 1.79 grams (85%), and the product had a melting point of 65.5° to 68.5° C. and an IR absorption peak at 1660 cm$^{-1}$ (c=0).

Some formulation examples will now be described. In the following Formulation Examples, compounds of this invention will be denoted by the compound numbers indicated above, and parts stand for "parts by weight" throughout all Examples.

FORMULATION EXAMPLE 1

Emulsion

Twenty grams of Compound No. 1 of the invention were dissolved in 73 parts of xylol, and added with 3 parts of polyoxyethylene alkyl ether, 3 parts of alkylbenzene sulfonate and 1 part of polyoxyethylenesorbitan alkylate, the latter three serving as emulsifiers, followed by sufficient mixing and stirring to obtain an emulsion.

FORMULATION EXAMPLE 2

Wettable Powder

To 40 parts of the Compound No. 1 of the invention were added 3 parts of white carbon, 50 parts of clay and additionally 3 parts of polyoxyethylene alkylaryl sulfonate and 4 parts of lignin sulfonate, the latter two being added as dispersion aids, and the whole mass was intimately mixed together followed by pulverization to prepare a wettable powder.

FORMULATION EXAMPLE 3

Powder

To 3 parts of Compound No. 1 of the invention were added 0.5 part of white carbon and 2.5 parts of clay, followed by mixing and pulverization. The pulverized product was then added to 94 parts of clay, and the whole mass was mixed intimately to obtain a powder.

Some Test Examples will now be set out below to verify that the compounds of the invention are utilizable as effective components in plant protection agents for control of fungi.

TEST EXAMPLE 1

Rice Sheath Bliqht

A formulated compound of the invention, formulated generally following the procedure as described in Formulation Example 2 to have a predetermined concentration, was spread in 9 cm diameter pots in which rice plants (Variety: KOSHIHIKARI) were cultivated to 5-leaf stage, the dose amount being 100 cc per 3 pots. After the lapse of one day from the spreading of the formulation, each third leaf sheath of the respective rice plants was inoculated with Rhizoctonia solani which had been cultivated on PDA cultivation medium, and then the pots were allowed to stand in a humidified chamber maintained at 25° C. After the lapse of 10 days, the length of the lesion formed on each leaf was measured, and the preventive value was calculated from the following equation.

| Preventive Value (%) = (1 − Length of Lesion, Treated Leaf Sheath/ Length of Lesion, Untreated Leaf Sheath) × 100 | | |
| --- | --- | --- |
| Compound | Concentration (ppm) | Preventive Value |
| 1 | 50 | 100 |
|  | 20 | 100 |
|  | 5 | 98 |
| 2 | 50 | 100 |
|  | 20 | 100 |
|  | 5 | 90 |
| A | 50 | 80 |
|  | 20 | 45 |

| -continued Preventive Value (%) = (1 − Length of Lesion, Treated Leaf Sheath/ Length of Lesion, Untreated Leaf Sheath) × 100 | | |
| --- | --- | --- |
| Compound | Concentration (ppm) | Preventive Value |
| | 5 | 25 |

Note:
Compound A was mepronil represented by the following formula:

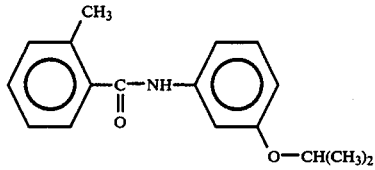

TEST EXAMPLE 2

Rice Sheath Blight

Rice plants (Variety: KOSHIHIKARI) were cultivated in a 1 m² concrete frame in the open air, and a formulation of a compound of this invention was sprayed by a hand-operated sprayer on the leaves of the cultivated rice plants at the panicle formation stage at a dose amount of 150 liters per 10 ares, the formulation being prepared generally following Formulation Example 2 to have a predetermined concentration. After one day from application of the compound of this invention, inoculum of rice straw medium was placed at the base of each rice hill. After cultivating for 25 days, the heights of the lesions of the respective rice plants were evaluated, and the preventive value was calculated from the following equation.

| Preventive Value (%) = (1 − Height of Lesion, Treated Leaf Sheath/ Height of lesion, Untreated Leaf Sheath) × 100 | | |
| --- | --- | --- |
| Compound | Concentration (ppm) | Preventive Value |
| 1 | 100 | 100 |
| | 50 | 100 |
| 2 | 100 | 100 |
| | 50 | 100 |
| A | 100 | 35 |
| | 50 | 15 |

Note: Compound A stands for mepronil.

TEST EXAMPLE 3

Wheat Brown Rust

A formulated compound of this invention having a predetermined concentration and prepared generally following the procedure as described in Formulation Example 2 was applied to a wheat variety (Variety: NORIN #61) grown in a 9 cm diameter pot, application being done by spray gan and the dose amount being 100 cc per 3 pots. Uredospore of Puccinia recodita were inoculated, and the pot was placed to stand in a humidified chamber for about 20 hours and then transferred to a green house, where it was kept for an additional 10 days. The number of lesions on each of the leaves was evaluated, and the preventive value was calculated from the following equation.

| Preventive Value (%) = (1 − Number of Lesion, Treated Leaf/ Number of Lesion, Untreated Leaf) × 100 | | |
| --- | --- | --- |
| Compound | Concentration (ppm) | Preventive Value |
| 1 | 50 | 100 |
| | 12.5 | 100 |
| | 2 | 100 |
| 2 | 50 | 100 |
| | 12.5 | 100 |
| | 2 | 100 |
| B | 50 | 90 |
| | 12.5 | 85 |
| | 2 | 20 |

Note:
Compound B was the compound disclosed in Japanese Patent Publication No. 12973/1978 and represented by the following formula:

TEST EXAMPLE 4

Wheat Brown Rust

A compound of this invention formulated generally following the procedure as described in Formulation Example 2 to have a predetermined concentration was applied to wheat plants (Variety: NORIN #61) grown in a field using a power style sprayer at a dose amount of 200 liters per 10 ares. Then, wheat plants with uredospore pustules were placed at each corner of the field immediately after foliar spray application of the fungicide candidates had been completed. After the lapse of 30 days from the foliar spray application, 20 wheat plants were randomly selected from each plot and their disease degrees were observed. The disease degrees of three higher rank leaves were evaluated with the standard of examination set as shown in the following Table, and the disease severity was calculated from the equation set forth below the Table.

| Disease Degrees | Number of Uredosori per Leaf |
| --- | --- |
| 0 | 0 |
| 1 | 1 to 5 |
| 2 | 6 to 12 |
| 3 | 13 to 25 |
| 4 | 26 to 50 |
| 5 | 51 to 100 |
| 6 | above 101 |

Disease Severity = (0xa + 1xb + 2xc ... + 6xg)/6xy; wherein a, b, c ... g each indicates the number of leaves having, respectively, the disease degrees of 0, 1, 2 ... 6; and y indicates the total number of examined leaves (namely, y = a + b + c + ... + g).

| Compound | Concentration (Density) | Disease Severity |
| --- | --- | --- |
| 1 | 2000 | 0.00 |
| 2 | 2000 | 0.03 |
| A | 1500 | 1.70 |
| Untreated | — | 4.20 |

Note: The compound A in the Table was mepronil.

As will be seen from Test Examples, the compounds of this invention exhibit superior preventive effects against various rusts, such as rice sheath blight or rusts of wheats, vegetables and ornamental plants.

We claim:

1. A plant protection agent for control of fungi represented by the following general formula:
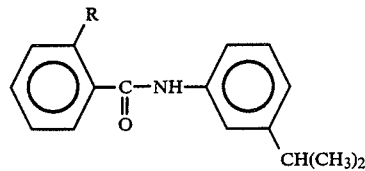
wherein R stands for a trifluoromethyl group.
2. A plant protection composition for the control of fungi comprising an effective amount of the compound claimed in claim 1 and an inert carrier.
* * * * *